United States Patent
Cho et al.

(10) Patent No.: US 8,353,843 B2
(45) Date of Patent: Jan. 15, 2013

(54) METHOD FOR PROVIDING CONTENTS AND ELECTRONIC DEVICE HAVING FUNCTION THEREFOR

(75) Inventors: Seong Moon Cho, Gyeonggi-do (KR); Youn Jae Lee, Seoul (KR); Vladimir Karyunovich Nagapetyan, Moscow (RU); Alexandr Nikolaevich Razumov, Moscow (RU); Viktoria Aslanbekovna Badtieva, Moscow (RU)

(73) Assignee: LG Electronics Inc., Seoul (KR)

( * ) Notice: Subject to any disclaimer, the term of this patent is extended or adjusted under 35 U.S.C. 154(b) by 1178 days.

(21) Appl. No.: 11/679,734

(22) Filed: Feb. 27, 2007

(65) Prior Publication Data
US 2007/0203421 A1   Aug. 30, 2007

(30) Foreign Application Priority Data
Feb. 27, 2006   (RU) ................................. 2006105801

(51) Int. Cl.
A61B 5/02   (2006.01)

(52) U.S. Cl. .......................... 600/508; 600/509; 600/514
(58) Field of Classification Search .................. 600/508, 600/514; 607/509
See application file for complete search history.

(56) References Cited

U.S. PATENT DOCUMENTS
5,267,942 A * 12/1993 Saperston ....................... 600/28

* cited by examiner

Primary Examiner — Nicole F Lavert
(74) Attorney, Agent, or Firm — Lee, Hong, Degerman, Kang & Waimey

(57) ABSTRACT

A method for providing contents and an electronic device having a function therefore is disclosed. The method comprises receiving information regarding a current heart rate of a user, selecting an audio file having a specific tempo determined in consideration of the current heart rate and a reference heart rate, and reproducing the selected audio file and a heartbeat sound reflecting the current heart rate simultaneously. Therefore, the heartbeat of the user may be effectively controlled.

36 Claims, 10 Drawing Sheets

FIG. 6

| DATE | I.D | 1st Session | 2nd Session | 3rd Session | REMARK |
|---|---|---|---|---|---|
| 04/2006 | 1. | Pulse-98<br>B.P.M.-90<br>Pulse-94 | Pulse-94<br>B.P.M.-84<br>Pulse-85 | Pulse-85<br>B.P.M.-80<br>Pulse-77 | Age:72<br>Gender:f |
| 04/2006 | 2. | Pulse-82<br>B.P.M.-78<br>Pulse-74 | Pulse-74 | | Age:54<br>Gender:f |
| 04/2006 | 3. | Pulse-88<br>B.P.M.-84<br>Pulse-80 | Pulse-80<br>B.P.M.-76<br>Pulse-76 | | Age:60<br>Gender:f |
| 04/2006 | 4. | Pulse-92<br>B.P.M.-84<br>Pulse-86 | Pulse-86<br>B.P.M.-80<br>Pulse-72 | | Age:55<br>Gender:f |
| 05/2006 | 5. | Pulse-86<br>B.P.M.-80<br>Pulse-78 | | | Age:43<br>Gender:m |
| 05/2006 | 6. | Pulse-84<br>B.P.M.-80<br>Pulse-80 | Pulse-80<br>B.P.M.-72<br>Pulse-72 | | Age:56<br>Gender:f |
| 05/2006 | 7. | Pulse-110<br>B.P.M.-106<br>Pulse-100 | Pulse-100<br>B.P.M.-92<br>Pulse-94 | Pulse-94<br>B.P.M.-84<br>Pulse-80 | Age:41<br>Gender:m |
| 05/2006 | 8. | Pulse-108<br>B.P.M.-100<br>Pulse-100 | Pulse-100<br>B.P.M.-92<br>Pulse-88 | Pulse-88<br>B.P.M.-82<br>Pulse-78 | Age:67<br>Gender:m |
| 05/2006 | 9. | Pulse-86<br>B.P.M.-84<br>Pulse-78 | | | Age:42<br>Gender:m |
| 05/2006 | 10. | Pulse-82<br>B.P.M.-78<br>Pulse-74 | | | Age:48<br>Gender:f |
| 05/2006 | 11. | Pulse-88<br>B.P.M.-84<br>Pulse-82 | Pulse-82<br>B.P.M.-76<br>Pulse-72 | | Age:54<br>Gender:f |
| 06/2006 | 12. | Pulse-102<br>B.P.M.-98<br>Pulse-96 | Pulse-96<br>B.P.M.-86<br>Pulse-84 | Pulse-84<br>B.P.M.-78<br>Pulse-72 | Age:40<br>Gender:f |

CURRENT HEART RATE — 1st Session column
TARGET HEART RATE — 3rd Session column

FIG. 7

|  |  |  | CURRENT HEART RATE | TARGET HEART RATE |  |
|---|---|---|---|---|---|
| DATE | I.D | Initial Pulse | 1st Session | 2nd Session | REMARK |
| 01/2007 | 1. | 84<br>T=(-4) | Pulse-84<br>B.P.M.-80<br>Pulse-80 | Pulse-80<br>B.P.M.-76<br>Pulse-80 | Age:51<br>Gender:f |
| 01/2007 | 2. | 80<br>T=(-6) | Pulse-80<br>B.P.M.-76<br>Pulse-74 |  | Age:54<br>Gender:f |
| 01/2007 | 3. | 82<br>T=(-4) | Pulse-82<br>B.P.M.-78<br>Pulse-78 | Pulse-78<br>B.P.M.-74<br>Pulse-78 | Age:49<br>Gender:f |
| 01/2007 | 4. | 78<br>T=(-4) | Pulse-78<br>B.P.M.-74<br>Pulse-74 |  | Age:55<br>Gender:f |
| 01/2007 | 5. | 82<br>T=(-4) | Pulse-82<br>B.P.M.-78<br>Pulse-78 | Pulse-78<br>B.P.M.-74<br>Pulse-78 | Age:43<br>Gender:f |

FIG. 8

|  |  |  | CURRENT HEART RATE | TARGET HEART RATE |  |
|---|---|---|---|---|---|
| DATE | I.D | Initial Pulse | 1st Session | 2nd Session | REMARK |
| 01/2007 | 1. | 84<br>T=(-10) | Pulse-84<br>B.P.M.-80<br>Pulse-78 | Pulse-78<br>B.P.M.-74<br>Pulse-74 | Age:51<br>Gender:m |
| 01/2007 | 2. | 82<br>T=(-6) | Pulse-82<br>B.P.M.-78<br>Pulse-76 |  | Age:54<br>Gender:f |
| 01/2007 | 3. | 88<br>T=(-12) | Pulse-88<br>B.P.M.-84<br>Pulse-80 | Pulse-80<br>B.P.M.-76<br>Pulse-76 | Age:49<br>Gender:f |
| 01/2007 | 4. | 82<br>T=(-6) | Pulse-82<br>B.P.M.-78<br>Pulse-78 | Pulse-78<br>B.P.M.-74<br>Pulse-76 | Age:38<br>Gender:f |
| 01/2007 | 5. | 86<br>T=(-10) | Pulse-86<br>B.P.M.-84<br>Pulse-76 |  | Age:44<br>Gender:f |

FIG. 9

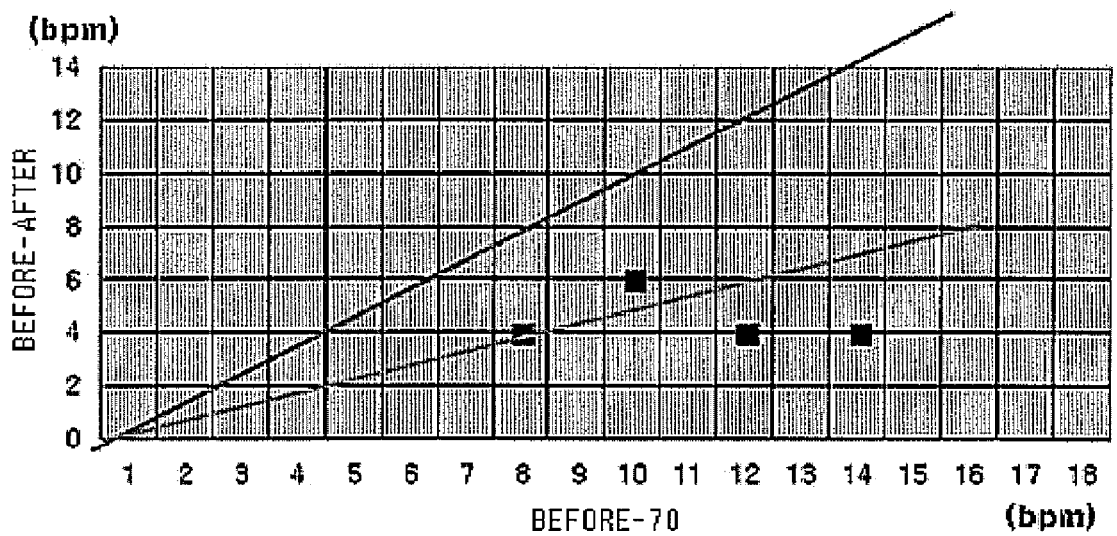

METHOD FOR PROVIDING CONTENTS AND ELECTRONIC DEVICE HAVING FUNCTION THEREFOR

CROSS-REFERENCE TO RELATED APPLICATION

The present application claims priority from Russian Patent Application No. 2006105801/14, filed Feb. 27, 2006, the entire contents of which is incorporated herein by reference.

BACKGROUND

1. Field of the Invention

The present invention relates to a method for providing contents and an electronic device having a function of providing contents, and more particularly to a method for providing contents and an electronic device having a function of providing contents for effectively controlling a heartbeat of a user in an irregular state into a normal state, and further for effectively changing a current heartbeat of a user into a target heartbeat.

2. Description of the Related Art

Recently, a variety of electronic devices with various functions comes to a market. Especially, due to development of audio processing technologies, a user may listen to music at any time and any place using a mobile terminal such as an MP3 Player or a cell phone.

Further, due to rapid progress of communication technologies, a variety of music files may be downloaded through wire or wireless communication networks. Thus, a user may listen to music using a mobile communication terminal even with a small capacity of memory without any difficulty.

However, general electronic devices do not provide a variety of contents suitable to their upgraded hardware and various needs of users in spite of the recent development of these technologies.

Especially for a mobile communication terminal, audio files are usually provided to be reproduced just for an entertainment without any specific purpose. There are few audio contents provided for a specific purpose other than the entertainment purpose.

SUMMARY

Accordingly, the present invention has been made to solve the above-mentioned problems occurring in the related art, and an object of the present invention is to provide a method for providing contents and an electronic device having a function of providing contents.

Additional advantages, objects and features of the invention will be set forth in part in the description which follows and in part will become apparent to those having ordinary skill in the art upon examination of the following or may be learned from practice of the invention.

In an aspect of the present invention, there is provided a method for providing contents using an electronic device, the method comprising: receiving information regarding a current heart rate of a user; selecting an audio file having a specific tempo determined in consideration of the current heart rate and a reference heart rate; and reproducing the selected audio file and a heartbeat sound reflecting the current heart rate simultaneously.

In another aspect of the present invention, there is provided an electronic device having a function of providing contents, the electronic device comprising: a heartbeat module for receiving information regarding a current heart rate of a user to output a heartbeat sound reflecting the current heart rate; a memory for storing information regarding reference heart rates; and a controller for reproducing an audio file having a specific tempo determined in consideration of the reference heart rate and the current heart rate and the heartbeat sound reflecting the current heart rate simultaneously.

In yet another aspect of the present invention, there is provided an electronic device having a function of providing contents, the electronic device comprising: a heartbeat module for receiving information regarding a current heart rate of a user; a memory for storing information regarding a reference heart rate and a plurality of audio files; and a controller for receiving information regarding the current heart rate by every predetermined period, to select an audio file having a specific tempo determined in consideration of the reference heart rate and the current heart rate, thereby reproducing the selected audio file, wherein the audio file having the specific tempo is automatically updated according to changes of the received information regarding the current heart rate by every predetermined period.

BRIEF DESCRIPTION OF THE DRAWINGS

The above and other objects, features and advantages of the present invention will be more apparent from the following detailed description taken in conjunction with the accompanying drawings, in which:

FIG. 6 is a table showing results of an experiment to which the method for providing contents according to the embodiment of the present invention is applied, FIG. 7 is a table showing results of an experiment to which only audio files are reproduced, FIG. 8 is a table showing results of an experiment to which both of audio files and heartbeat sounds are reproduced, FIGS. 9 and 10 are graphs corresponding to the results of FIGS. 7 and 8, respectively.

DETAILED DESCRIPTION

Figure 1:
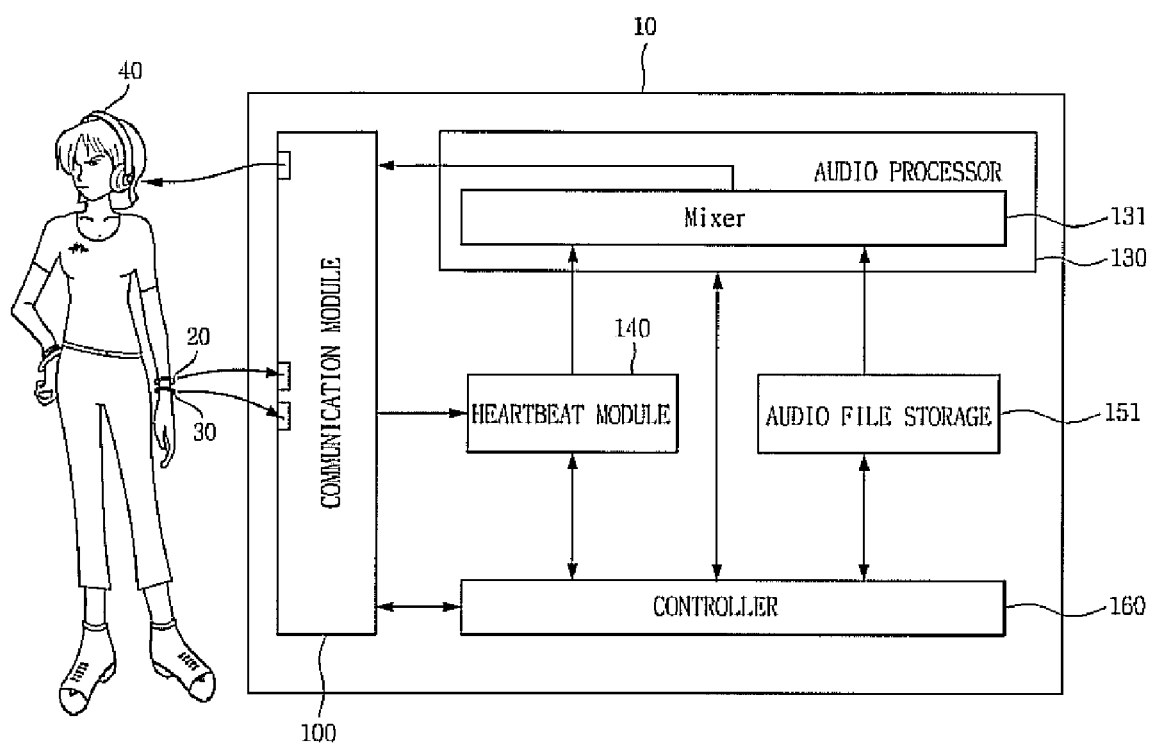
FIG. 1 is a schematic view illustrating an electronic system for providing contents according to an embodiment of the present invention.

The aspects and features of the present invention and methods for achieving the aspects and features will be apparent by referring to the embodiments to be described in detail with reference to the accompanying drawings. However, the present invention is not limited to the embodiments disclosed hereinafter, but can be implemented in diverse forms. The matters defined in the description, such as the detailed construction and elements, are nothing but specific details provided to assist those of ordinary skill in the art in a comprehensive understanding of the invention, and the present invention is only defined within the scope of the appended claims. In the entire description of the present invention, the same drawing reference numerals are used for the same elements across various figures.

Hereinafter, embodiments of the present invention will be described in detail with reference to the accompanying drawings.

Figure 2:
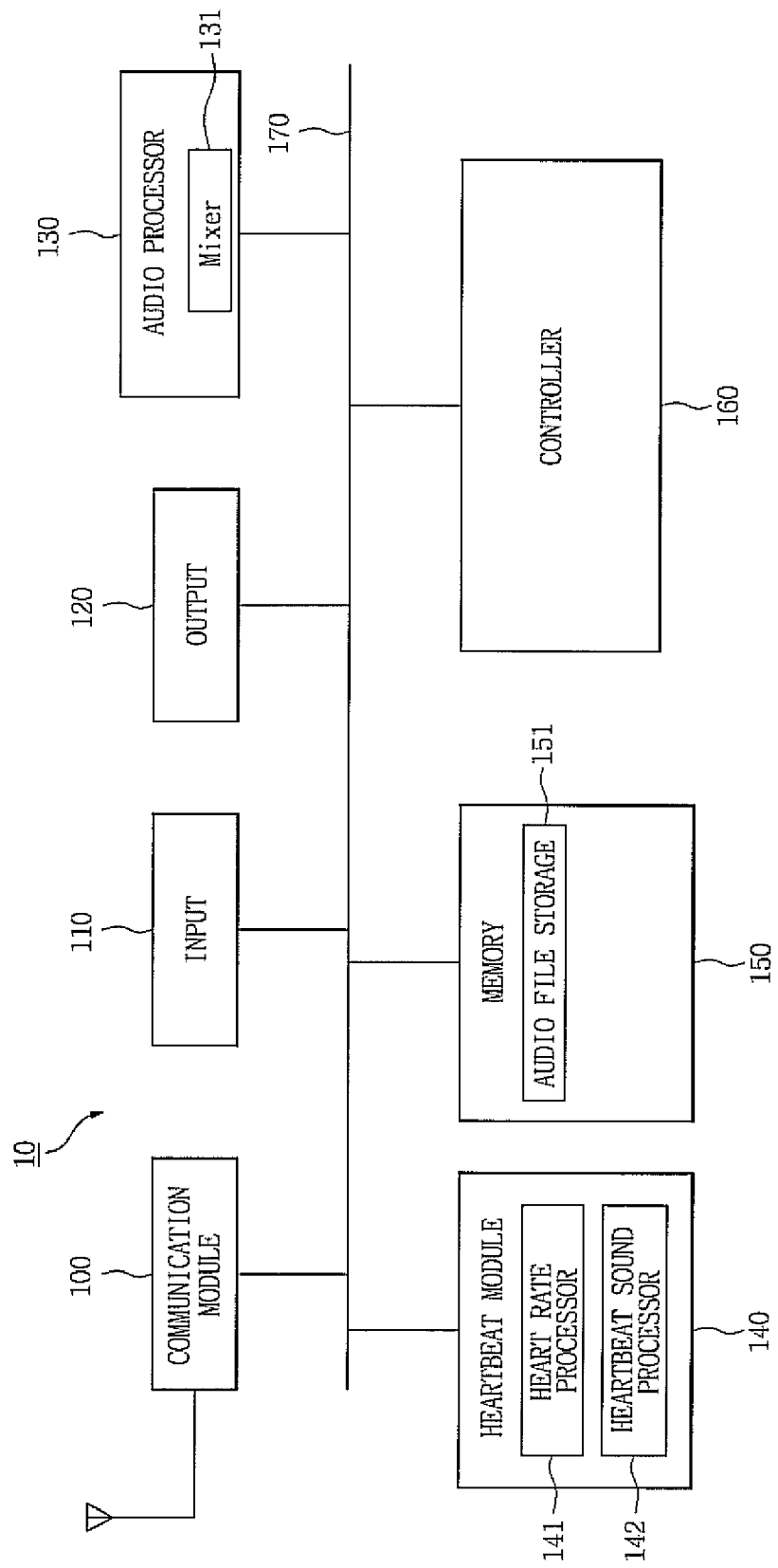
FIG. 2 is a block diagram illustrating an electronic device having a function for providing contents according to the embodiment of the present invention.

FIG. 1 is a schematic view illustrating an electronic system for providing contents according to an embodiment of the present invention, and FIG. 2 is a block diagram illustrating an electronic device having a function for providing contents according to the embodiment of the present invention.

Hereinafter, the electronic device and the electronic system for providing contents according to the embodiment of the present invention will be described in detail with reference to FIGS. 1 and 2.

Referring to FIGS. 1 and 2, the electronic system may comprise a heart rate measurement device 20 and a heartbeat sound acquisition device 30 in addition to the electronic device 10.

The heart rate measurement device 20 is attached to a body of a user to measure a heart rate of the user.

The heartbeat sound acquisition device 30 is attached to the body of the user to acquire a heartbeat sound of the user.

The heart rate measurement device 20 and the heartbeat sound acquisition device may be integrated in one body.

Alternatively, at least one of the heart rate measurement device 20 and the heartbeat sound acquisition device may be incorporated in a body of the electronic device 10 in a sensor form.

On the other hand, the electronic device 10 may analyze the heartbeat sound from the heartbeat acquisition device 30 to calculate a heart rate of the user. In this case, the heart rate measurement device 20 is not a necessary element.

Further, the heartbeat sound acquisition device is not a necessary element for implementing the present invention, which will be described later.

The electronic device 10 comprises a communication module 100, an input 110, a display 120, an audio processor 130, a heartbeat module 140, a memory 150 and a controller 160. These elements are connected to each other through a bus 170.

The communication module 100 transmits and receives data outside of the electronic device 10 via wire or wireless communication manner. In more detail, the communication module 100 transmits and receives data with the heart rate measurement device 20 and the heartbeat sound acquisition device 30. To this end, the communication module 100 may adopt wire or wireless communication. In case of wire communication, the communication module 10 may utilize a short distance wireless communication technology such as Bluetooth, Infrared Data Association (IrDA) and Zigbee. These technologies are well known and thus a detailed description thereof will be omitted here.

The communication module 100 may include a mobile communication module for transmitting and receiving data through a mobile communication network. The mobile communication module is for functions such as audio/video communications and message services.

The input 110 may include a touch screen or a key pad having a plurality of number keys and direction keys to input various information and commands from a user.

The audio processor 130 processes audio signals including signals from a micro phone MIC to output the processed audio signals through a speaker SPK. Moreover, the audio processor 130 may process audio signals to be output to the microphone MIC for informing results of various processing or control operations, and may process audio signals with respect to various information and commands input from the microphone MIC.

The audio processor 130 may include a mixer 131 for mixing at least two audio signals from different audio sources.

The heartbeat module 140 processes information regarding a heartbeat of the user to transmit the processed information to the controller 160.

The heartbeat module 140 may include a heart rate processor 141 and a heartbeat sound processor 142.

The heart rate processor 141 processes information regarding a heart rate received from the heart rate measurement device 20.

The heartbeat sound processor 142 processes information regarding a heartbeat sound received from the heartbeat sound acquisition device 30.

The memory 150 stores programs for controlling overall operations of the electronic device 10, and various data inputted, processed and outputted during the overall operations of the electronic device under the control of the controller 160.

Especially, the memory 150 may include an audio file storage 151 for storing at least one audio file. The audio file may be downloaded from a specific server providing multimedia contents via wire or wireless communication networks. Further, the audio file may have information regarding tempo. The information regarding tempo may be presented in terms of beats per minute (bpm).

The audio file storage 151 may classify the stored at least one audio file into a plurality of BPM groups, each of them having a different range of tempo. For example, the group A may contain a plurality of audio files having 81 to 90 bpm, and the group B may contain a plurality of audio files having 91 to 100 bpm.

The memory 150 may further store information regarding reference heart rates which will be described later.

The controller 160 controls the above described elements including overall operations of the electronic device 10 according to the embodiment of the present invention.

As described above, the electronic device 10 may include the heart rate measurement device 20 and the heartbeat sound acquisition device 30 in sensor forms.

Alternatively, the electronic device 10 may receive a heartbeat sound of a user from the heartbeat sound acquisition device 30 and analyze the received heartbeat sound to calculate a heart rate of the user.

The electronic device 10 according to the embodiment of the present invention can be implemented in various electronic devices such as a mobile phone, an MP3 player, a personal digital assistant (PDA), a portable multimedia player, and a home network system.

Figure 3:
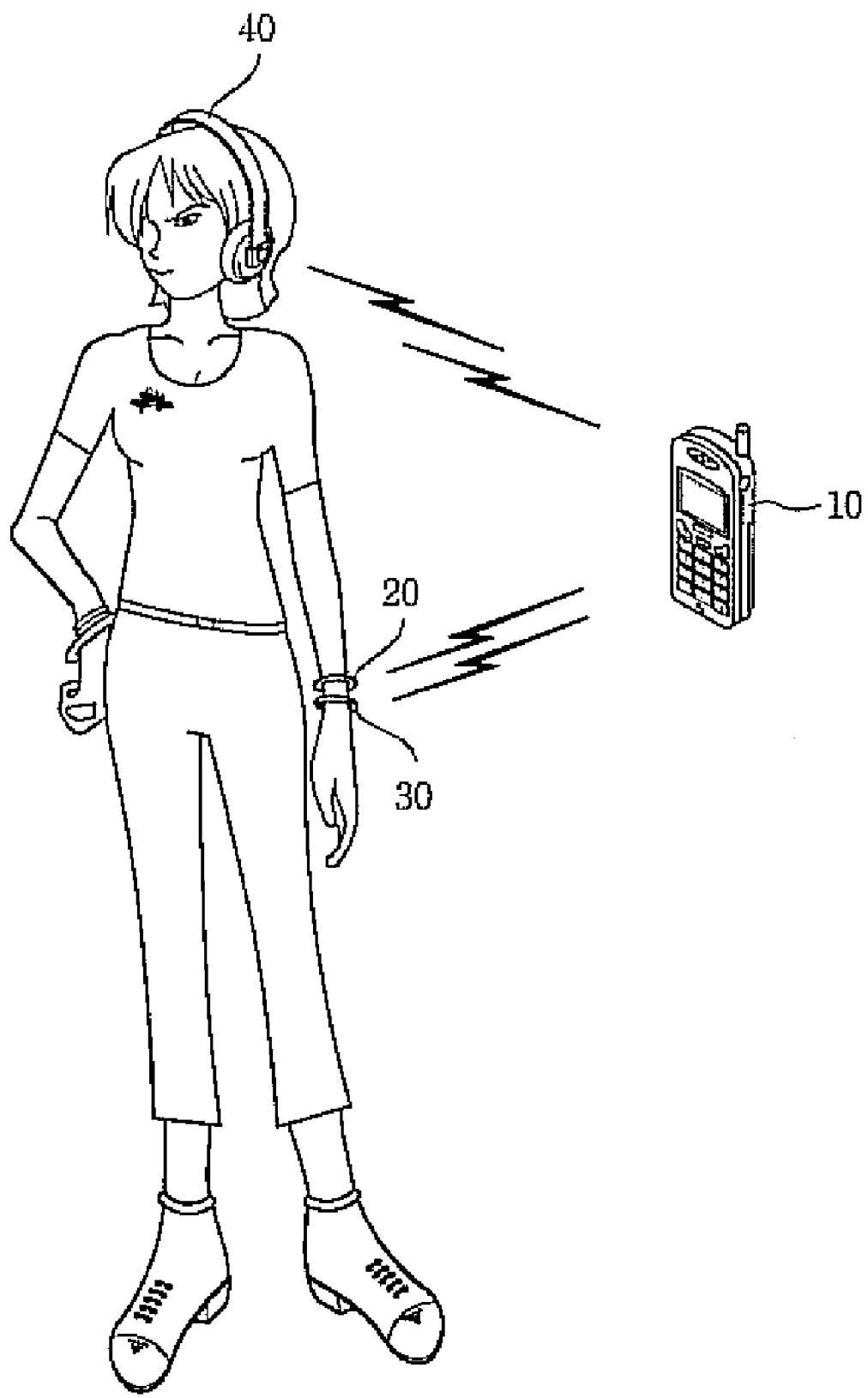
FIGS. 3 and 4 are examples, to which the electronic device according to the embodiment of the present invention is implemented.
Figure 4:
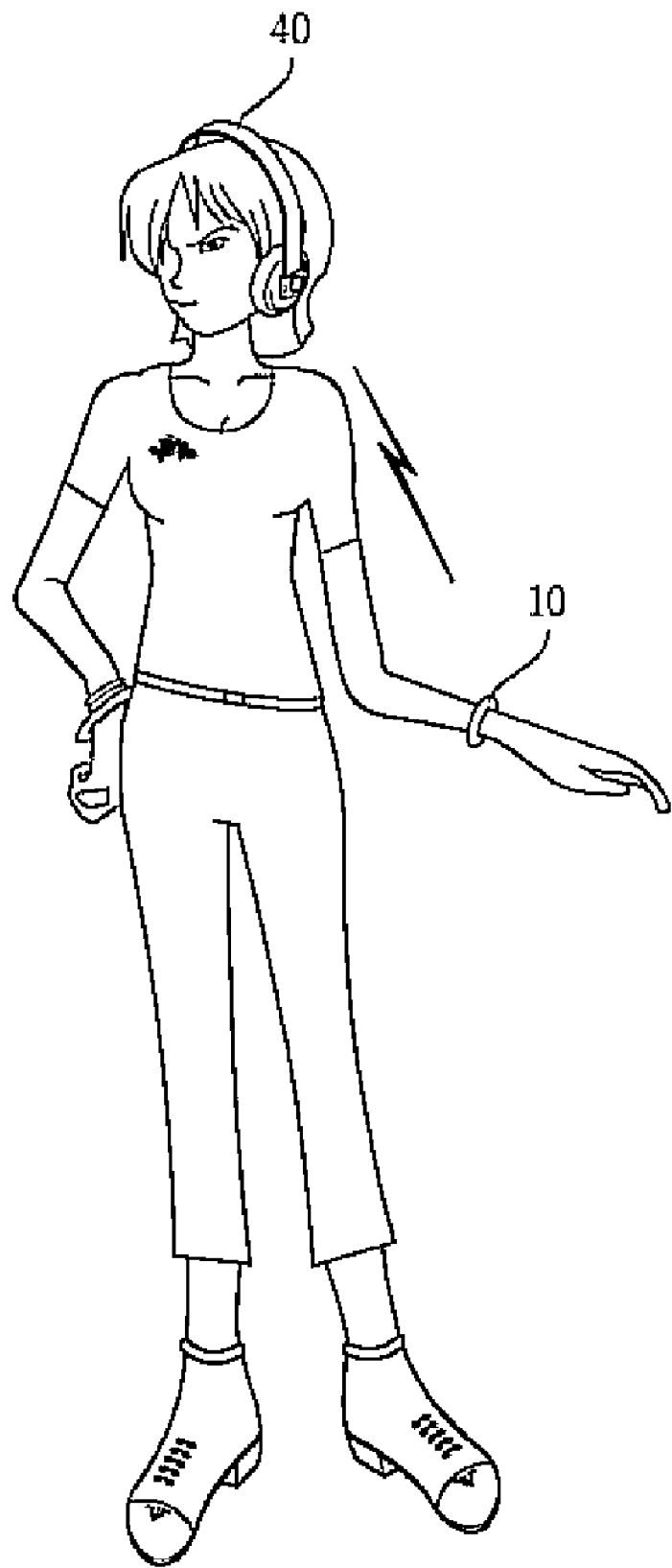

FIGS. 3 and 4 are examples, to which the electronic device according to the embodiment of the present invention is implemented.

Referring to FIG. 3, the electronic device 10 is implemented in a mobile phone. The mobile phone may utilize the communication module 100 to transmit and receive data with the heart rate measurement device 20, the heartbeat sound acquisition device 30, and a head set 40 through a short distance communication such as Bluetooth.

Referring to FIG. 4, the electronic device 10 is implemented in a wrist attachable electronic device. In FIG. 4, the electronic device includes the heart rate measurement device 20 and the heartbeat sound acquisition device 30 in one body. The electronic device of FIG. 4 may be attached to a wrist of a user, thus the heart rate measurement device 20 and the heartbeat sound acquisition device 30 may be attached to the wrist of the user to acquire information regarding a heart rate and heartbeat sound therefrom. The electronic device 10 may utilize the communication module 100 to communicate with a head set 40 through a short distance communication.

Figure 5:
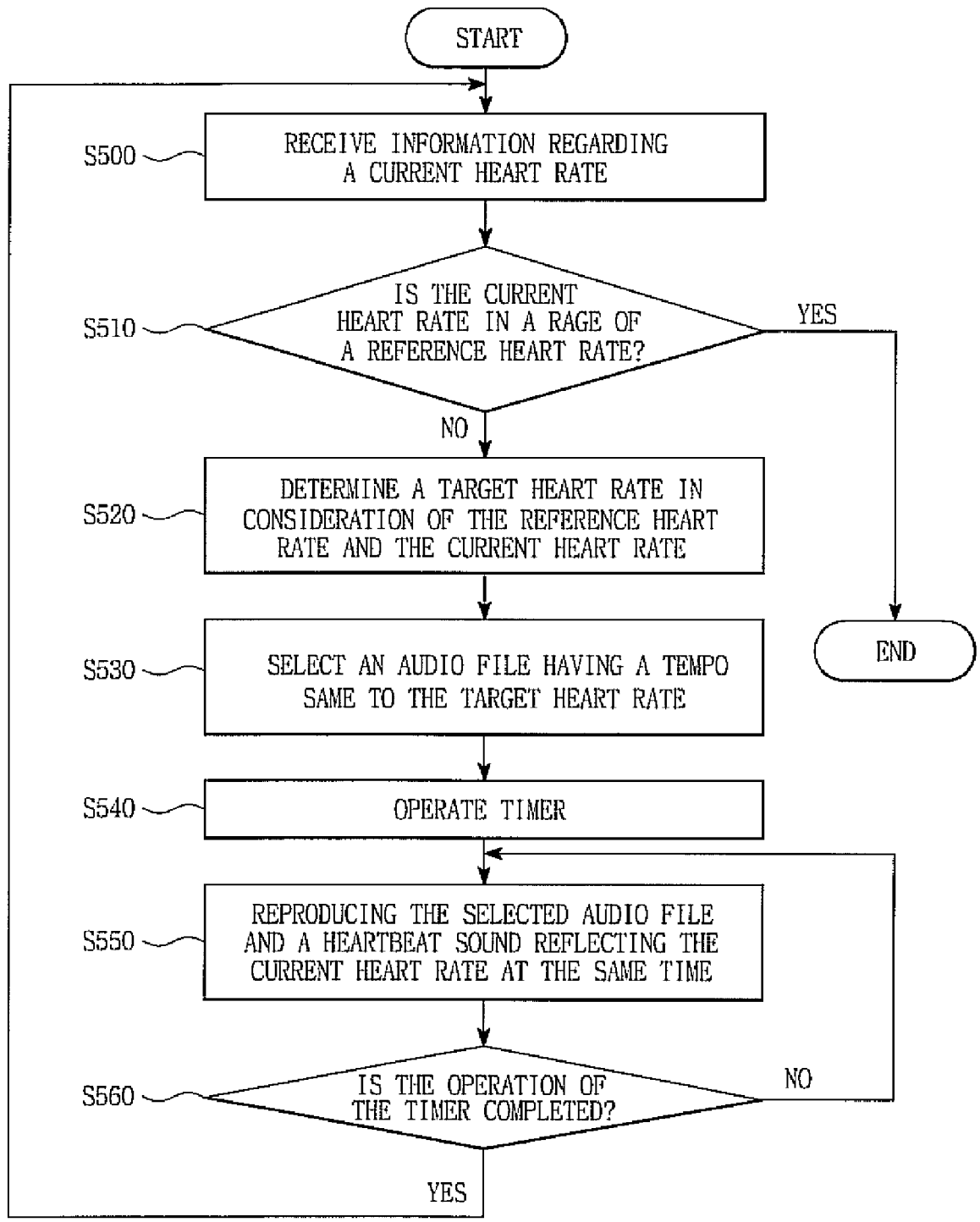
FIG. 5 is a flow chart illustrating a method for providing contents according to the embodiment of the present invention.

FIG. 5 is a flow chart illustrating a method for providing contents according to the embodiment of the present invention. The method for providing contents according to the embodiment of the present invention may be implemented using the electronic device 10 described above with reference to FIGS. 1 to 4. Hereinafter, the method for providing contents and operations of the electronic device 10 therefor will be described in detail with reference to FIGS. 1 to 5.

At first, the heart rate processor 141 receives information regarding a current heart rate of a user(S). For example, the heart rate measurement device 20 may measure the current heart rate of the user. The heart rate processor 141 receives the current heart rate from the heart rate measurement device 20. As described above, the heart rate measurement device 20 may be implemented in a sensor form, or separated from the electronic device 10.

The controller 160 determines whether the current heart rate is in a range of a reference heart rate (S510). As described above, information regarding the reference heart rates may be stored at the memory 150. Alternatively, information regarding the reference heart rates may be set or changed by the user. For example, the user may input the information regarding the reference heart rates through the input 110.

Generally, a normal heart rate of an adult is known to be in a rage of 60 to 80 bpm. However, the reference heart rates of present invention are not limited to the above normal heart rate. As described above, the reference heart rates may be input by the user, and thus may vary as set by the user. For example, it is common knowledge that a heart rate during an exercise has to be higher than the normal heart rate to achieve an effect of the exercise. In this case, the user may set the reference heart rate for the exercise to fall in a range of 75 to 95 bpm which is higher than the above rage of 60 to 80 for the normal heart rate in ways to measure or enhance the effect of the exercise. Alternatively, the reference heart rate for the exercise may be set to a medically or physically recommended heart rate. Therefore, the user can effectively exercise while experiencing a proper physical load corresponding to physical conditions of the user.

When it is determined that the current heart rate is not in the range of the reference heart rate at step S510, the controller 160 determines a target heart rate in consideration of the reference heart rate and the current heart rate (S520). The target heart rate may be set to a certain value between the reference heart rate and the current heart rate. For example, let's assume that the current heart rate is 100 bpm and the range of the reference heart rate is 60 to 90 bpm. In this example, the target heart rate may be set to a certain value between 100 and 80 bpm, and the current heart rate and the highest value in the range of the reference heart rate, respectively. There may be various ways to decide which value between the reference heart rate and the current heart rate to be the target heart rate. For example, the target heart rate may be decided using a 4 bpm unit. That is, the target heart rate of the above example may be decided to be 96 bpm which is 4 bpm lower than the current heart rate 100 bpm. Alternatively, the target heart rate may be decided to be the reference heart rate when a difference between the current heart rate and the reference heart rate is not significant.

The controller 160 selects an audio file having a tempo same to the decided target heart rate within an error range. The error range may be set or changed. For example, when the target heart rate is set to be 96 bpm and the error range is set to be 2 bpm, the controller 160 retrieves an audio file having a tempo of 94 to 98 bpm. If a plurality of audio file having tempos of 94 to 98 bpm are retrieved, then the controller 160 may choose one audio file having the tempo closest to the target heart rate. Further, if a plurality of audio files having tempos same to the target heart rate are retrieved, then the controller 160 may randomly choose one audio file.

In case that the audio files stored at the audio file storage 151 include information regarding tempo, the controller may use this information to perform the above S530 step.

However, in case that the audio files stored at the audio file storage 151 do not include information regarding tempo, the controller 160 may calculate tempos with respect to the audio files to perform the above step S530. Otherwise, the controller 160 may previously analyze tempos with respect to the audio files stored at the audio file storage 151, whereby store information regarding to the analyzed tempos at the memory 150 in connection with the respective audio files.

As described above, when the audio files are classified into the plurality of BPM groups having different ranges of tempos to be stored at the storage 151, the controller 160 may select an audio file having a specific tempo in consideration of the BPM group classification. For example, when the specific tempo is decided to be 95 bpm, a specific audio file in the BPM group of 95 bpm may be selected. Using the BPM groups, it can be easy to manage the audio files and the speed of retrieving the audio file can be accelerated.

Accordingly, the controller 160 operates a timer during a predetermined reproducing period (S540), and reproduces the selected audio file and a heartbeat sound reflecting the current heart rate (S550).

The predetermined reproducing period is a time period for the audio file and the heartbeat sound to be reproduced. For example, the predetermined reproducing period may be set to be 3 to 5 minutes.

The heartbeat sound reflecting the current heart rate is a heartbeat sound reproduced in a tempo same to the current heart rate received at the step S500, or a heartbeat sound of the user which may vary in real time. That is, sources for the heartbeat sound reproduced at the step S550 may be classified to 2 different sources.

Firstly, the source for the heartbeat sound may be the heartbeat sound received by the heartbeat sound processor 142 from the heartbeat sound acquisition device 30, that is, the heartbeat sound of the user. The real heartbeat sound of the user is acquired to be reproduced, thus the heartbeat sound to be reproduced may reflect the heart rate of the user and may vary in real time.

Secondly, the source for the heartbeat sound may be a predetermined audio data stored at the electronic device 10 in advance. At the step S550, since the heartbeat sound is reproduced in beat so as to reflect the current heart rate of the user, the source for the heartbeat sound has not necessarily to be the real heartbeat sound of the user. Thus, the controller 160 may reproduce the predetermined audio data in a tempo same to the current heart rate. Further, the controller 160 may receive heart rates of the user in real-time and may vary the tempo of the reproduced audio data in accordance with the received heart rates to achieve a same effect of the real heartbeat sound of the user. The predetermined audio data may be stored at the memory 150 or the heartbeat sound processor 142.

The controller 160 determines whether the operation of the timer is completed (S560). Upon determining the operation of the timer is completed, the controller 160 returns to the step S500. As the steps S500 to S560 is repeatedly performed, the current heart rate of the user may fall into the range of the reference heart rate. Through these repeated procedure, the electronic device 10 may continuously receive feedback of a condition of the user such as a heart rate by every predetermined period in real-time, to provide corresponding contents in consideration of the feedback condition.

On the other hand, when it is determined that the current heart rate is in the range of the reference heart rate at step S510, the controller 160 may reproduce an audio file having a tempo in the range of the reference heart rate. At this time, the controller 160 may reproduce a heartbeat sound reflecting the current heart rate and the audio file simultaneously.

The controller 160 may control the display 120 during any of the steps S500 to S560 to display information visually showing a procedure of the method for providing contents according to the present invention. For example, information regarding to the current heart rate, the reference heart rate, the target heart rate and the heartbeat sound may be displayed at the display 120.

The controller 160 may control the display 120 during the step S550 to display a predetermined video information determined according to a tempo level of the reproduced audio file or a level of the current heart rate. For example, when the current heart rate is in a higher level than the reference heart rate, the display 120 may be controlled to display a still picture or a moving picture for visually providing the user of senses of stability and comfort. A typical example for this end may be a still picture of a family and a moving picture with a background of the nature. For another example, when the current heart rate is in a lower level than the reference heart rate, the display 120 may be controlled to display a still picture or a moving picture for exciting the user or for provoke a laugh visually. A typical example for this end may be a moving picture of a comedy. Therefore, an effect sought by the present invention may be effectively achieved through a visual stimulation provided along with an auditory stimulation according to the embodiment of the present invention.

The audio file selected to be reproduced at the step S550 may be reproduced in a tempo input from the input 110 by the user. For example, if the user wants to change the tempo of the currently reproduced audio according to the embodiment of the present invention, then the user may input a tempo through the input 110 to change the tempo of the currently reproduced audio.

In the above described embodiment of the present invention, the target heart rate is set to be lower than the current heart rate for firstly providing contents to the user.

However, an audio file having the tempo same to the current heart rate of the user may be reproduced not to stimulate the user, and consequently audio files according to target heart rates determined to be lower than the current heart rate may be reproduced as the steps S500 to S560 being repeatedly performed. Thus, a physical rhythm of the user may be controlled naturally in stages so that the current heart rate reaches the target heart rate. When the current heart rate of the user is not in the range of the reference heart rate, thereby an audio file having a tempo near to the reference heart rate and the heartbeat sound are simultaneously reproduced, the user may experience discomfort at first as if hearing a dissonance. However, as the current heart rate approaches the tempo of the audio file, the user may feel comfort.

Cases of Tachyarrhythmia and Bradyarrhythmia

The method for providing contents according to the embodiment of the present invention is highly effective for cases of irregularity or malfunction related to a heartbeat. For example, the method for providing contents according to the embodiment of the present invention may be used for a patient suffered from arrhythmia or in an instant arrhythmia state. Arrhythmia may be divided into tachyarrhythmia defined by a heart rate higher than 100 bpm and bradyarrhythmia defined by a heart rate lower than 60 bpm.

For example, the method for providing contents may be implemented for the case of tachyarrhythmia through a following procedure.

When a current heart rate of a user is 100 bpm, the method for providing contents according to the embodiment of the present invention may be performed to decrease the current heart rate to a reference heart rate of 80 bpm. To this end, the method for providing contents of the embodiment of the present invention may be performed repeatedly a few times, since the user may not biologically adapt to the target heart rate determined to be much lower than the current heart rate.

That is, the target heart rate may need to be determined step by step. For example, the target heart rate for a first session may be determined to be 106 bpm which is 4 bpm lower than the current heart rate 110 bpm. For a second session, when a current heart rate newly received at the step S500 is 107 bpm, a target heart rate determined at the step S520 may be 103 bpm in consideration of 107 bpm.

This approach may consider biological adaptability of the user to gradually decrease the current heart rate of the user into the range of the reference heart rate.

For another example, the method for providing contents according to the embodiment of the present invention may be implemented for the case of bradyarrhythmia similarly to the above described case of tachyarrhythmia. The target heart rate may be determined to be higher than the current heart rate of the user for example. As an audio file having a tempo same to the target heart rate is reproduced simultaneously with a heartbeat sound reflecting the current heart rate of the user, the current heart rate of the user may reach the determined target heart rate.

FIG. 6 is a table showing results of an experiment to which the method for providing contents according to the embodiment of the present invention is applied. Hereinafter, the experiment of FIG. 6 will be described.

In this experiment, the above described method for providing contents according to the embodiment of the present invention is performed not more than 3 times for each user. If a current heart rate of a certain user reaches a range of a reference heart rate, 60 to 80 bpm, then sessions for the certain user may be terminated after the method is performed once or twice. Otherwise, a new target heart rate is determined for a next session to be performed when the current heart rate does not reach the target heart rate determined at a current session.

Referring to FIG. 6, a current heart rate measured from a user of I.D. 1 at a first session is 98 bpm and a target heart rate determined in consideration of the current heart rate and a reference heart rate, for example, 60 to 80 bpm is 90 bpm. The electronic device 10 reproduces an audio file having a tempo same to the target heart rate and a heartbeat sound simultaneously during a predetermined period. At the end of the first session, a measured current heart rate of the user 1 is 94 bpm, that is, the target heart rate 90 bpm and the reference heart rate 80 bpm is not achieved and, therefore, a second session is performed.

As described above, an audio file having a predetermined tempo and a heartbeat sound reflecting a current heart rate of a user are simultaneously reproduced according to the method for providing contents of the embodiment of the present invention. This is because the results thereof may be significantly effective than those of a case that only an audio file is reproduced.

Figure 10:
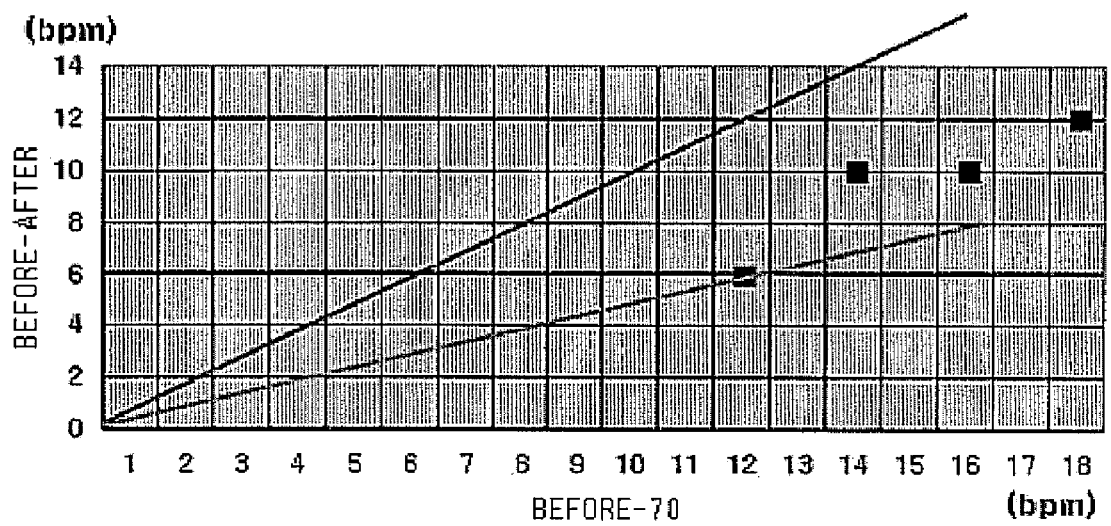

FIG. 7 is a table showing results of an experiment to which only audio files are reproduced, and FIG. 8 is a table showing results of an experiment to which both of audio files and heartbeat sounds are reproduced. FIGS. 9 and 10 are graphs corresponding to the results of FIGS. 7 and 8, respectively. Referring to FIGS. 7 to 10, the method for providing contents according to the embodiment of the present invention will be described in comparison to a method for providing contents as reproducing only an audio file. Herein, cases of FIGS. 7 and 8 with respect to the user with I.D 1 will be compared to each other, in which experiment conditions for two cases are the same.

1$^{st}$ Session

The current heart rate and the target heart rate for the first session are 84 and 80 bpm, respectively for the cases of FIGS. 7 and 8. Referring to FIG. 7, a current heart rate is 80 at the end of the first session, that is, the current heart rate is decreased 4 bpm from the current heart rate 84 bpm at the beginning of the first session. Referring to FIG. 8, a current heart rate is 78 at the end of the first session, that is, the current heart rate is decreased 6 bpm from the current heart rate 84 bpm at the beginning of the first session.

2$^{nd}$ Session

The second session is started when the first session is ended and results of the second session are follows: Referring to FIG. 7, there is no changes in the current heart rate 80 bpm at the end of the second session and at the beginning of the second session. Meanwhile, the current heart rate 78 bpm is decreased to a target heart rate 74 bpm.

In fact, it can be known that the method for providing contents by reproducing an audio file and a heartbeat sound simultaneously according to the embodiment of the present invention is significantly effective than the method for providing contents by reproducing only an audio file. This is much clearer if comparing cases of FIGS. 9 and 10. Horizontal axes for FIGS. 9 and 10 represent difference between the current heart rates and the target heart rates before the experiments, and vertical axes represent difference between the current heart rates before and after the experiments. Comparing the cases of FIGS. 9 and 10, results of FIG. 10 indicated by rectangular marks are much more effective that those of FIG. 9.

Figure 11:
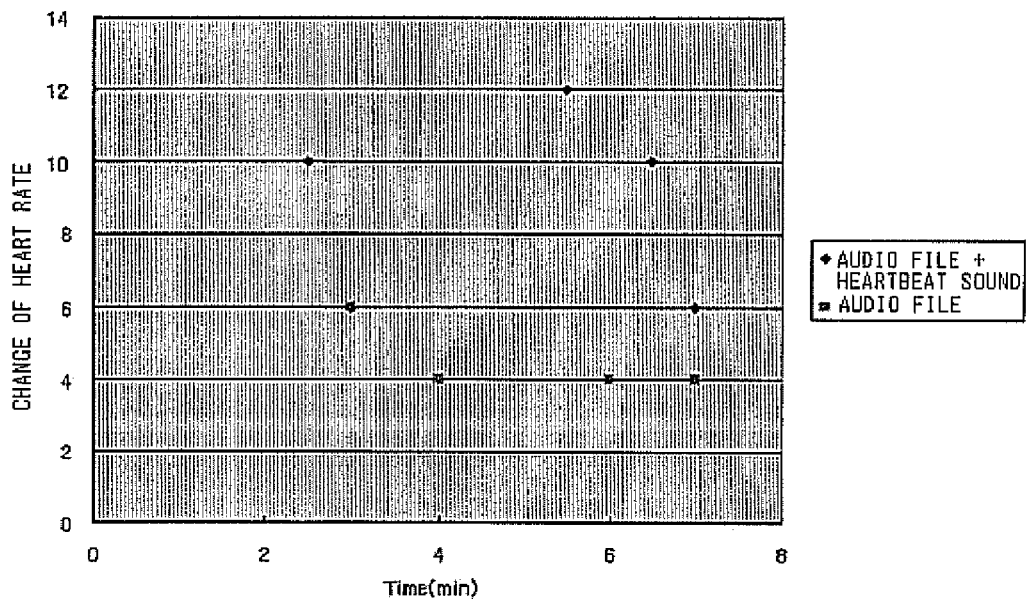
FIG. 11 is a graph drawn in correspondence with a table 1.

A following table 1 shows changes of heart rates for case 1 that an audio file and a heartbeat sound are reproduced simultaneously and for case 2 that only an audio file is reproduced. A following table 2 shows a data analyzing reproducing periods against changes of heart rates using the data of table 1. FIG. 11 is a graph drawn in correspondence with table 1.

TABLE 1

| session | (1) audio file + heartbeat sound | | (2) audio file | |
|---|---|---|---|---|
| | Reproducing period (min) | Heart rate change (bpm) | Reproducing period (min) | Heart rate change (bpm) |
| 1 | 2.5 | 10 | 3 | 6 |
| 2 | 5.5 | 12 | 4 | 4 |
| 3 | 6.5 | 10 | 6 | 4 |
| 4 | 7 | 6 | 7 | 4 |

TABLE 2

Reproducing period against heart rate change (min/bpm) = reproducing period (min)/heart rate change (bpm)

| Session | (1) audio file + heartbeat sound | (2) audio file |
|---|---|---|
| 1 | 0.25 | 0.50 |
| 2 | 0.46 | 1.00 |

TABLE 2-continued

Reproducing period against heart rate change (min/bpm) = reproducing period (min)/heart rate change (bpm)

| Session | (1) audio file + heartbeat sound | (2) audio file |
|---|---|---|
| 3 | 0.65 | 1.50 |
| 4 | 1.12 | 1.75 |
| Average | 0.62 | 1.19 |

As shown in tables 1 and 2, and FIG. 11, heart rates are changed more rapidly in the case that an audio file and a heartbeat sound are reproduced simultaneously than the case that only an audio file is reproduced. That is, the reproducing period needed for a unit heart rate change, 1 bpm, is about 0.6 minute (1) when an audio file and a heartbeat sound are reproduced simultaneously while the reproducing period is about 1.2 (2) when only an audio file is reproduced. Therefore, it can be known that the method for providing contents by reproducing an audio file and a heartbeat sound simultaneously according to the embodiment of the present invention is significantly effective to control the heart rate than the method for providing contents by reproducing only an audio file.

The above described embodiment of the present invention is mainly for the method for providing contents and the electronic device having the function therefore. However, the technical scope of the present invention will not be limited thereto.

Figure 12:
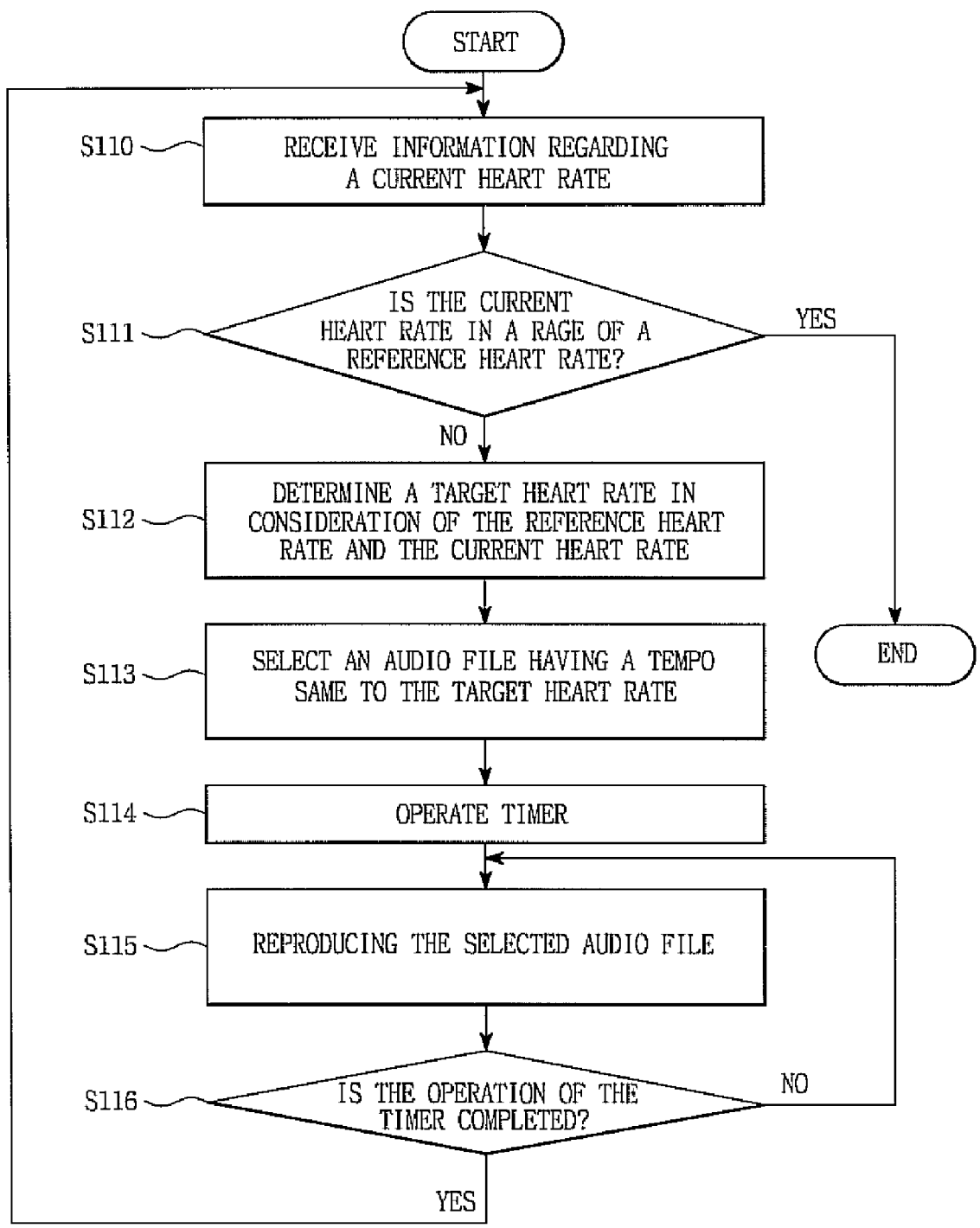
FIG. 12 is a flow chart illustrating a method for providing contents according to another embodiment of the present invention.

FIG. 12 is a flow chart illustrating a method for providing contents according to another embodiment of the present invention.

Referring to FIG. 12, only the step S115 is different from the step S550 of FIG. 5. Namely, according to the another embodiment of the present invention, only an audio file selected in accordance with the above described embodiment of the present invention may be reproduced without reproducing of a heartbeat sound reflecting the current heart rate of the user at the step 5115. At this time, as the user listens to the reproduced audio file during a predetermined period, the current heart rate of the user may reach a tempo of the reproduced audio file.

When an operation of the timer is completed (S116), the method returns to the step S110 for receiving information regarding a new current heart rate, and performs the rest steps. Therefore, an audio file selected at the step S113 may reflect a current heart rate of the user in real-time or updated periodically.

In conclusion, the method for providing contents according to the another embodiment of the present invention may update an audio file to be reproduced to promote the control of the heartbeat of the user until the current heart rate of the user reaches a range of a reference heart rate, thereby providing the user with a convenient interface.

The above describe method for providing content according to the another embodiment of the present invention may be performed using the above described electronic device 10.

However, the mixer 131 and the heartbeat sound processor may be omitted from the electronic device 10 shown in FIGS. 1 and 2, since a heartbeat sound is not necessarily reproduced. The rest elements are the same to the electronic device 10 shown in FIGS. 1 and 2, thus the detailed description thereof will be omitted herein. The electronic device to implement the method for providing content according to the another embodiment of the present invention may be implemented to various electronic devices as shown in FIGS. 3 and 4.

The above described electronic device having function for providing contents according to the embodiments of the present invention may further provide user interfaces to implement the method for providing contents according to the embodiments of the present invention. For example, the user interfaces may provide menu structures and screens to implement the method for providing contents according to the embodiments of the present invention. The more detailed description of the user interfaces will be omitted herein.

The method for providing contents according to embodiments of the present invention may be implemented in computer readable media recording programs to execute the steps of the method.

Firstly, according to the embodiments of the present invention, a heartbeat of a user may be controlled effectively.

Secondly, according to the embodiments of the present invention, a heartbeat of a user in an irregular state may be turned to a normal state.

Thirdly, according to the embodiments of the present invention, a current heartbeat state of a user may be changed to a target heartbeat state. For example, as adapting the embodiments of the present invention for an exercise, the user can effectively exercise while experiencing a proper physical load corresponding to physiological conditions of the user.

Fourthly, according to the embodiments of the present invention, contents may be provided in consideration of a heartbeat state feedback periodically in real-time.

The embodiments of the present invention have been described for illustrative purposes, and those skilled in the art will appreciate that various modifications, additions and substitutions are possible without departing from the scope and spirit of the invention as disclosed in the accompanying claims. Therefore, the scope of the present invention should be defined by the appended claims and their legal equivalents.

What is claimed is:

1. A method for providing contents using an electronic device, the method comprising:
   receiving information regarding a current heart rate of a user;
   determining a target heart rate having a value between the current heart rate and a reference heart rate when the current heart rate is not within a specific range of the reference heart rate;
   selecting an audio file having a first tempo determined in consideration of the current heart rate and the reference heart rate; and
   reproducing, through a speaker connected to the electronic device, the selected audio file simultaneously with a heartbeat sound that reflects the current heart rate,
   wherein the reproduced heartbeat sound has a second tempo that corresponds to the current heart rate, and
   wherein the first tempo of the selected audio file is different from the second tempo of the heartbeat sound when the current heart rate is not in a specific range of the target heart rate.

2. The method of claim 1, wherein the reference heart rate is settable by the user.

3. The method of claim 1, wherein the current heart rate is obtained from the user.

4. The method of claim 1, wherein the first tempo of the selected audio file is within a predetermined error range of the target heart rate.

5. The method of claim 1, wherein the audio file is stored at a memory of the electronic device.

6. The method of claim 1, wherein the audio file is provided from a contents providing server outside the electronic device.

7. The method of claim 1, wherein the heartbeat sound is obtained from the user in real-time.

8. The method of claim 1, wherein the heartbeat sound is reproduced in the second tempo corresponding to the current heart rate using a predetermined heartbeat sound previously stored.

9. The method of claim 1, further comprising displaying predetermined picture information determined according to a level of the current heart rate or a level of the first tempo.

10. The method of claim 1, wherein the receiving of the information is repeated by every predetermined period.

11. The method of claim 1, wherein reproducing the selected audio file simultaneously with the heartbeat sound comprises producing a dissonant sound when the first tempo of the selected audio file is within the specific range of the reference heart rate and the heartbeat sound is not within the specific range of the reference heart rate.

12. The method of claim 4, wherein the target heart rate is redetermined in consideration of the reference heart rate and the current heart rate if the current heart rate fails to reach the reference heart rate after reproducing the audio file and the heartbeat sound for a predetermined period of time.

13. A non-transitory computer program product, comprising: a non-transitory computer readable medium comprising: code for causing a computer to receive information regarding a current heart rate of a user; code for causing the computer to determine a target heart rate with a value between the current heart rate and a reference heart rate when the current heart rate is not within a specific range of the reference heart rate; code for causing the computer to select an audio file having a first temp determined in consideration of the current heart rate and the reference heart rate; and code for causing the computer to reproduce, through a speaker connected to the electronic device, the selected audio file simultaneously with a heartbeat sound that reflects the current heart rate, wherein the reproduced heartbeat sound has a second tempo that corresponds to the current heart rate, and wherein the first tempo of the select audio file is different from the second tempo of the heartbeat sound when the current heart rate is not a specific range of the target heart rate.

14. An electronic device having a function of providing contents, the electronic device comprising:
   a heartbeat module for receiving information regarding a current heart rate of a user in order to output a heartbeat sound reflecting the current heart rate;
   a memory for storing information regarding reference heart rates; and
   a controller for determining a target heart rate having a value between the current heart rate and a reference heart rate when the current heart rate is not within a specific range of the reference heart rate, wherein the controller reproduces, through a speaker connected to the electronic device, the heartbeat sound simultaneously with an audio file having a first tempo determined in consideration of the reference heart rate and the current heart rate,
   wherein the heartbeat sound has a second tempo that corresponds to the current heart rate, and
   wherein the first tempo of the audio file is different from the second tempo of the heartbeat sound when the current heart rate is not within a specific range of the target heart rate.

15. The electronic device of claim 14, wherein the memory stores at least one audio file and the controller selects the audio file having the first tempo among the stored at least one audio file.

16. The electronic device of claim 15, wherein the controller classifies the at least one audio file into a plurality of groups having different bpm (beats per minute) to be stored in the memory, and the controller selects the audio file having the first tempo with reference to the plurality of groups.

17. The electronic device of claim 14, further comprising a communication module wherein the audio file is provided from a contents providing server outside the electronic device through the communication module.

18. The electronic device of claim 14, wherein the first tempo of the audio file is within a predetermined error range of the target heart rate.

19. The electronic device of claim 14, wherein the heartbeat module receives information regarding the current heart rate of the user from an external heart rate measurement device.

20. The electronic device of claim 14, wherein the heartbeat module receives information regarding the current heart rate of the user from an internal heart rate measurement sensor.

21. The electronic device of claim 14, wherein the heartbeat sound is acquired from an external heartbeat sound acquisition device attachable to a body of the user in real-time.

22. The electronic device of claim 14, wherein the heartbeat sound is acquired from an internal heartbeat sound acquisition sensor capable of contact with a body of the user in real-time.

23. The electronic device of claim 14, wherein the heartbeat sound is reproduced using predetermined audio sources previously stored in the memory.

24. The electronic device of claim 14, further comprising an input module for inputting the information regarding the reference heart rate.

25. The electronic device of claim 14, further comprising a display for displaying at least one of the information regarding the current heart rate, the information regarding the reference heart rates, information regarding the heartbeat sound and information regarding the audio file under a control of the controller.

26. The method of claim 14, wherein the controller reproduces the heartbeat sound simultaneously with the audio file as a dissonant sound when the first tempo of the audio file is within the specific range of the reference heart rate and the heartbeat sound is not within the specific range of the reference heart rate.

27. The electronic device of claim 18, wherein the target heart rate is redetermined in consideration of the reference heart rate and the current heart rate if the current heart rate fails to reach the reference heart rate after reproducing the audio file and the heartbeat sound for a predetermined period of time.

28. An electronic device having a function of providing contents, the electronic device comprising:
    a heartbeat module for receiving information regarding a current heart rate of a user;
    a memory for storing information regarding a reference heart rate and a plurality of audio files; and
    a controller for receiving information regarding the current heart rate at a predetermined period, determining a target heart rate having a value between the current heart rate and the reference heart rate when the current heart rate is not within a specific range of the reference heart rate, selecting an audio file from the plurality of audio files having a first tempo determined in consideration of the reference heart rate and the current heart rate, and reproducing the selected audio file,
    wherein the controller reproduces, through a speaker connected to the electronic device, the selected audio file simultaneously with a heartbeat sound that reflects the current heart rate,
    wherein the heartbeat sound has a second tempo corresponding to the current heart rate,
    wherein the selected audio file having the first tempo is automatically updated according to changes in the received information regarding the current heart rate at each predetermined period, and
    wherein the first tempo of the selected audio file is different from the second tempo of the heartbeat sound when the current heart rate is not within a specific range of the target heart rate.

29. The electronic device of claim 28, wherein the first tempo of the selected audio file is within a predetermined error range of the target heart rate.

30. The electronic device of claim 28, wherein the heartbeat module receives information regarding the current heart rate of the user from an external heart rate measurement device.

31. The electronic device of claim 28, wherein the heartbeat module receives information regarding the current heart rate of the user from an internal heart rate measurement sensor.

32. The electronic device of claim 28, wherein the heartbeat sound is acquired from an external heartbeat sound acquisition device attachable to a body of the user in real-time.

33. The electronic device of claim 28, wherein the heartbeat sound is acquired from an internal heartbeat sound acquisition sensor capable of contact with a body of the user in real-time.

34. The electronic device of claim 28, wherein the heartbeat sound is reproduced through predetermined audio sources previously stored in the memory.

35. The method of claim 28, wherein the controller reproduces the selected audio file simultaneously with the heartbeat sound as a dissonant sound when the first tempo of the selected audio file is within the specific range of the reference heart rate and the heartbeat sound is not within the specific range of the reference heart rate.

36. The electronic device of claim 29, wherein the target heart rate is redetermined in consideration of the reference heart rate and the current heart rate if the current heart rate fails to reach the reference heart rate after reproducing the audio file and the heartbeat sound for a predetermined period of time.

* * * * *